United States Patent
Vaisnys et al.

(10) Patent No.: US 8,888,737 B2
(45) Date of Patent: Nov. 18, 2014

(54) METHOD AND APPARATUS FOR CARDIAC TISSUE MONITORING AND CATHETER-BASED PERFUSION FOR MITIGATING ACUTE REOXYGENATION INJURY

(75) Inventors: Gintaras A. Vaisnys, Chicago, IL (US); Neil J. Thomas, Chicago, IL (US); James G. Moore, Guilford, CT (US)

(73) Assignee: Rheoxtech, LLC, Chicago, IL (US)

( * ) Notice: Subject to any disclaimer, the term of this patent is extended or adjusted under 35 U.S.C. 154(b) by 733 days.

(21) Appl. No.: 12/582,515

(22) Filed: Oct. 20, 2009

(65) Prior Publication Data
US 2011/0092951 A1 Apr. 21, 2011

(51) Int. Cl.
*A61M 31/00* (2006.01)
*A61M 1/36* (2006.01)

(52) U.S. Cl.
CPC .............. *A61M 1/36* (2013.01); *A61M 1/3613* (2013.01); *A61M 2202/0476* (2013.01); *A61M 2230/00* (2013.01)
USPC ............ 604/66; 604/6.14; 604/890.1; 422/45

(58) Field of Classification Search
CPC ................ A61M 2001/3613; A61M 2230/205
USPC ................... 604/6.14, 66, 503, 890.1; 422/45
See application file for complete search history.

(56) References Cited

U.S. PATENT DOCUMENTS

| | | | |
|---|---|---|---|
| 4,466,804 A | 8/1984 | Hino | |
| 4,540,399 A | 9/1985 | Litzie et al. | |
| 5,011,469 A | 4/1991 | Buckberg et al. | |
| 5,322,500 A | 6/1994 | Johnson et al. | |
| 5,725,492 A | 3/1998 | Igo et al. | |
| 5,770,073 A | 6/1998 | Bach et al. | |
| 5,895,578 A | 4/1999 | Simard et al. | |
| 5,935,093 A | 8/1999 | Elgas et al. | |
| 6,039,078 A | 3/2000 | Tamari | |
| 6,071,258 A | 6/2000 | Dalke et al. | |
| 6,248,087 B1 | 6/2001 | Spears et al. | |
| 6,387,323 B1 | 5/2002 | Afzal et al. | |
| 6,443,609 B2 | 9/2002 | Short | |
| 6,454,999 B1 | 9/2002 | Farhanginia et al. | |
| 6,607,698 B1 | 8/2003 | Spears et al. | |
| 6,613,008 B2 | 9/2003 | Aboul-Hosn et al. | |

(Continued)

FOREIGN PATENT DOCUMENTS

| EP | 0357338 A2 | 3/1990 |
|---|---|---|
| FR | 2513884 A | 4/1983 |

(Continued)

OTHER PUBLICATIONS

Supplementary Partial European Search Report dated Feb. 20, 2007.

(Continued)

*Primary Examiner* — Emily Schmidt
(74) *Attorney, Agent, or Firm* — King & Spalding LLP

(57) ABSTRACT

A system and methods are described for improving the management of ischemic cardiac tissue during acute coronary syndromes or other ischemic conditions. A method and apparatus is described that allows mitigation of oxygen-related injury by precisely modulating the level of oxygen re-exposure during reoxygenation by a controlled feedback loop based on parameters of the tissue measured by a real-time tissue sensor or probe.

10 Claims, 5 Drawing Sheets

(56) References Cited

U.S. PATENT DOCUMENTS

| | | |
|---|---|---|
| 6,730,267 B2 | 5/2004 | Stringer et al. |
| 6,746,417 B2 | 6/2004 | Spears et al. |
| 6,918,887 B1 | 7/2005 | Gremel et al. |
| 6,974,435 B2 | 12/2005 | Daw et al. |
| 7,022,099 B2 | 4/2006 | Litzie et al. |
| 7,455,812 B2 | 11/2008 | Thomas |
| 2002/0085952 A1 | 7/2002 | Ellingbee et al. |
| 2003/0023230 A1 | 1/2003 | Lewis et al. |
| 2005/0063860 A1 | 3/2005 | Carpenter et al. |
| 2005/0084416 A1 | 4/2005 | Thomas |
| 2005/0203292 A1* | 9/2005 | Kuppusamy et al. ......... 540/122 |
| 2006/0100639 A1* | 5/2006 | Levin et al. ................... 606/106 |
| 2006/0258981 A1 | 11/2006 | Eidenschink |
| 2007/0041909 A1 | 2/2007 | Kupussamy et al. |
| 2008/0171726 A1 | 7/2008 | Roth et al. |

FOREIGN PATENT DOCUMENTS

| | | | |
|---|---|---|---|
| FR | 2648714 A1 | 12/1990 | |
| WO | WO 99/08733 A1 | 2/1999 | |
| WO | WO 99/08734 A1 | 2/1999 | |
| WO | WO 00/16825 A1 | 3/2000 | |
| WO | WO 00/47266 A1 | 8/2000 | |
| WO | WO 03/070300 A1 | 8/2003 | |
| WO | WO 2008/148062 | * 12/2008 | ............... A61B 5/02 |

OTHER PUBLICATIONS

Thomas, N. "Controlled Cardiac Reoxygenation in Adults with Ischemic Heart Disease,", The Journal of Thoracic and Cardiovascular Surger, Mar. 1999.

Ihnken et al., "Normoxic Cardiopulmonary Bypass Reduces Oxidatave Myocardial Damage and Nitric Oxide During Cardiac Operations in the Adult," Cardiovascular Surgery, 1998, vol. 116, No.2.

Ihnken et al., "Delayed Cardioplegic Reoxygenation Reduces Reoxygenation Injury in Cyanotic Immature Hearts," the Society of Thoracic Surgeons, 1998.

Allen et al., "Detrimental Effects of Cardiopulmonary Bypass in Cyanotic Infants: Preventing the Reoxygenation Injury," The Society of Thoracic Surgeons, 1997.

"CDI Systems 500 GUI," http://www.idsa.org/whatis/seewhat/idea99/winners/cdi500gui.htm., Dec. 17, 2002.

"3M Wins Medical Design Excellence Award for Blood Parameter Monitoring Device," http://3m.com/profile/pressbox/cdiaward.html., May 17, 1999.

"Cardioplegia Volume Tracking Feature Adds Convenience, Value to 3M Sarns System 8000," http://3m.com/profile/pressbox/cardiop.html., Jul. 24, 1996.

* cited by examiner

410

420

430

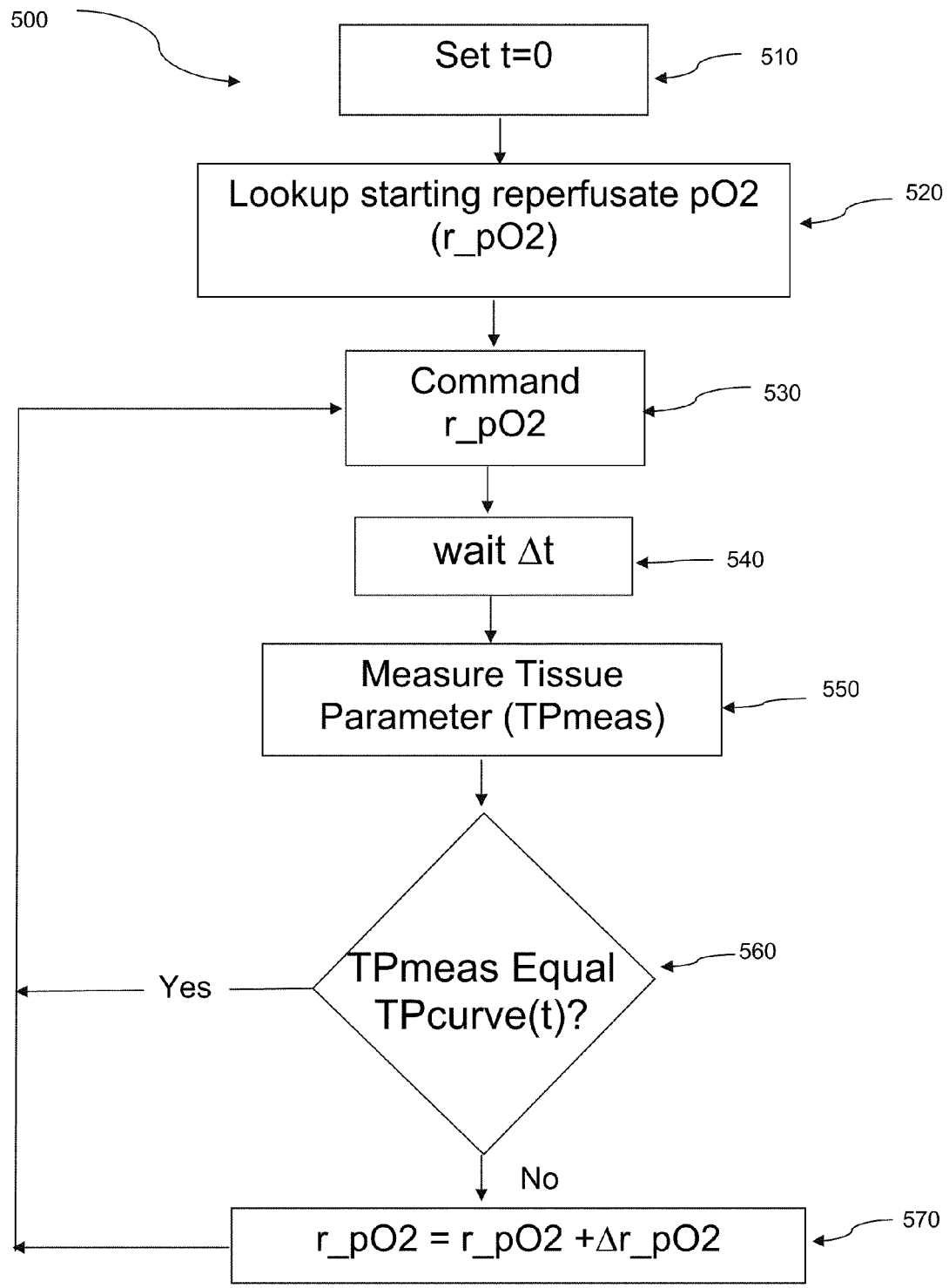

METHOD AND APPARATUS FOR CARDIAC TISSUE MONITORING AND CATHETER-BASED PERFUSION FOR MITIGATING ACUTE REOXYGENATION INJURY

FIELD OF THE INVENTION

The invention relates to the clinical arena of interventional cardiology and, in particular, the field of percutaneous coronary interventions and treatments for acute coronary syndrome (including acute myocardial infarction and/or unstable angina). A method and apparatus is described that provides the ability to mitigate oxygen-related injury by modulating the level of oxygen re-exposure during reperfusion using a feedback loop that provides information regarding the condition of the tissue being addressed.

BACKGROUND

Considerable effort and resources have been devoted to reducing the burden of cardiovascular disease and mortality rates after acute myocardial infarction have decreased over the past 30 years. However, coronary artery disease remains the leading cause of morbidity and mortality in the developed world. An estimated 79.4 million American adults (1 in 3) have one or more types of cardiovascular disease. Of these, an estimated 1.4 million Americans per year will have a myocardial infarction and another 500,000 present with other forms of acute coronary events that lead to cardiac ischemia. In 2007, an estimated 1.68 million patients were discharged in the US suffering from acute coronary syndrome. In 2004, an estimated 6,363,000 in-patient cardiovascular operations and procedures were performed in the United States. These included an estimated 1,285,000 in-patient angioplasty procedures, 427,000 in-patient bypass procedures and 1,471,000 in-patient diagnostic cardiac catheterizations (see Rosamond et al. (2007) Heart Disease and Stroke Statistics—2007 Update. *Circulation*. 115:e69-3171).

For patients who suffer from any form of acute coronary syndrome, the heart muscle is deprived of adequate levels of oxygen until appropriate treatment can be initiated. The deprivation can occur for a variable period of time and along a spectrum of severity. In many cases, irreversible damage to the heart can result in infarction, with cell death occurring in one of more areas of the left ventricular or right ventricular myocardium or within the conduction system of the heart. In addition to the effects of this lack of available oxygen on cardiomyocytes and conduction tissue, it has become increasingly recognized that the endothelial cells lining the blood vessels can also be damaged or can become impaired in their ability to function. Furthermore, the recognition of the importance of the endothelial lining of the vasculature has allowed a broader understanding of the resultant microvascular dysfunction that can follow even successful reperfusion of the epicardial or larger arterial or arteriolar supply. This also highlights the need for more appropriate means by which to mitigate post-ischemic patterns of injury.

In human beings with acute coronary insufficiency, ischemia is usually not limited merely to the area supplied by an artery affected by acute occlusion.

Modern treatment of acute myocardial infarction or myocardial ischemia often comprises performing percutaneous intervention on the vessels to facilitate increased blood flow. Coronary interventions typically include procedures that generally require advancing a guiding wire through an artery into a region of obstruction; advancing a catheter including a dilation device such as a balloon over that wire through the offending lesion; and then inflating the device, i.e. the angioplasty balloon, to eliminate the lesion. After deflation, the artery is then open to existing blood flow. Other methods of eliminating lesions include angioplasty with stent deployment, directional atherectomy with or without distal protection, laser therapy, intracoronary declotting and ultrasound devices. Such procedures can all be broadly considered to be part of the clinical arena of percutaneous coronary intervention (PCI).

In the setting of acute coronary events, current ACC/AHA guidelines regarding acute percutaneous coronary interventions exist to determine the timing, among other clinically relevant parameters, of PCI and to steer the operator to (or away from) the heart catheterization lab. These guidelines are based upon the "clinical condition" of the patient and focus largely upon the appearance of an EKG, time from onset of symptoms, the clinical appearance of the patient, including hemodynamic parameters, and, sometimes, other "thrombolysis in myocardial infarction" trial (TIMI) risk factors defined a decade or longer ago. Although guided by well-defined and well-studied clinical indicators, the clinical assessment of a patient with an acute evolving coronary syndrome is known to be imprecise. Often times, a patient may be unclear on when the syndrome began, may have mistaken his or her symptoms for a different condition and may have even attributed them incorrectly to something unrelated to the heart. An assessment of the time from the onset of symptoms and the amount of time that may elapse between the patients' arrival to emergency care and the inflation of an angioplasty balloon can often only be estimated and is highly variable. This lack of precision can predispose to significant, additive cardiac injury that relates to both the inciting syndrome and the approach taken by the clinician. One unintended consequence of the comparatively successful and widespread catheter-based treatment of such acute coronary conditions has been an increase in chronic heart failure related to ischemic cardiac injury. This syndrome is otherwise known as ischemic cardiomyopathy and represents the most common form of congestive heart failure in the U.S. and the developed world in patients with associated left ventricular systolic impairment. Heart failure specialists have, for years; pointed out that in the modern era we have exchanged a reduction in death from acute myocardial infarction for an epidemic of chronic congestive heart failure.

Without modification, the goal of acute PCI therapy during acute coronary events is to reestablish normal blood flow in the narrowed or occluded artery. However, it has become clear that immediate reperfusion with arterial blood in certain circumstances causes extensive, and potentially lethal, reperfusion injury. In fact, because of the realization of the potential for such injury, many patients for whom this invention will benefit would not otherwise be offered immediate reperfusion therapy. Such patients are those in whom the coronary syndrome is known to have been progressing for a considerable period of time. Time to reperfusion, as a result, has become a benchmark standard in the treatment of many such patients. If too much time has elapsed, many patients are treated medically, allowed to "cool-off" and, if they survive, are approached much later after significant damage to the "tissue at risk" has occurred.

Reoxygenation injury can occur after reestablishing blood flow (perfusion) in a previously ischemic tissue. The severity of the ischemic conditions sets the stage for significant oxygen-related and other damage depending upon certain conditions that exist once flow is reestablished or ischemia is eliminated. Even a brief period of abrupt oxygen re-exposure after ischemia can initiate damaging oxidative stress and result in numerous inflammatory responses. Key calcium ion fluctuations triggered by the presence of molecular oxygen that lead to various degrees of contracture can also occur. Countless other molecular mechanisms and pathways, are also involved and may lead to both immediate and delayed cellular injury and swelling within the cytosolic, mitochondrial and sarcoplasmic reticular membranes and can ultimately lead to incremental or catastrophic cellular damage or death. Our understanding in this regard points to thousands of years of evolving mechanisms for tolerating ischemic injury that can be harmful upon exposure to abrupt reperfusion initiating by modern treatment modalities.

Although, several methods have been proposed to combat the effects of this pattern of oxygen and reperfusion-related injury, these have been either misguided or ineffective. For examples, proposed methods includes those aimed at supplying superoxygenated fluids to previously ischemic tissue (see for eg. U.S. Patent Publication No. 2005/0042132) to "force" oxygen into the damaged areas, or methods of reducing the temperature of the reperfusion fluids to reduce metabolic load of the cells. None of these methods has offered a realizable approach to actually preventing or reducing reperfusion-related injury in the population of patients most seriously affected by acute ischemia.

Certain groups have proposed feedback systems to guide reperfusion therapy. For example, U.S. Pat. No. 5,533,957 to Aldea provides a retroperfusion catheter that can be adjusted based on pressure feedback. Similarly, U.S. Pat. No. 6,481,439 to Salient Interventional Systems, Inc. and related cases provide catheters that allow feedback control of a reperfusate based on pressure of the downstream fluids. U.S. Pat. No. 7,218,964 and related cases to Medtronic provide a closed loop system for providing electrical stimulation to the spinal cord to regulate the autonomic nervous system. U.S. Patent Publication No. 2007/0169779 to Freeman provides an apparatus for resuscitating a patient using a ventilator adjustable based on certain tissue parameters. U.S. Patent Publication No. 2006/0142826 to Willard provides a system for targeted delivery of supercooled fluids that can be regulated based on temperature feedback. U.S. Patent Publication No. 2006/0100639 to Levin provides certain methods in which reperfusion therapy is delivered to the patient based on pressure feedback. However, these feedback systems limited to pressure or temperature concerns of the perfusate.

There remains a need for improved methods and apparatus to reduce reperfusion injury. There specifically remains a need for a method and apparatus that provides improved control over tissue conditions that can be linked to catheter-based therapies that do not require surgery or as an adjunct to myocardial protection strategies used during open-heart surgery and acute coronary bypass surgery.

It is therefore an object of the present invention to provide improved methods and apparatuses for controlled reoxygenation of ischemic tissue. It is another object of the invention to reduce reperfusion injury and provide improved patient outcome across a broader spectrum of the population being treated for acute coronary syndrome.

SUMMARY OF THE INVENTION

The present invention is based on a recognition that reoxygenation of previously ischemic tissues should be carefully modulated in response to local tissue conditions and guided by the dynamic changes that occur upon manipulation of the circulatory system. It is not generally appreciated that such manipulation (either mechanical or pharmacologic) can directly impact the local tissue condition by altering both supply of, and demand for, oxygen at the level of the individual cells and the tissue as a whole. The methods and apparatus described herein directly address the need to be responsive to the actual conditions within the local environment of the ischemic tissue by using sensors or probes to measure the condition of the tissue affected by the ischemic insult and then control reperfusion in response to the changing conditions of that ischemic tissue.

Accordingly, in one embodiment, the invention provides a method of treatment of an ischemic tissue comprising measuring local tissue conditions in a host and modulating oxygen levels of a reperfusate being delivered to the host based on the measurement. The measurement of tissue condition is accomplished using a tissue condition monitor. The tissue condition monitor is linked, directly or indirectly, to a reperfusion controller that controls the oxygen content of a perfusate generated by a reperfusion generator. The controller modulates the reperfusion generator in response to a signal from the tissue condition monitor to deliver differing levels of oxygenated fluid to the ischemic tissue. In this embodiment the controller may modify oxygen level of the reperfusate based upon a pre-set algorithm or protocol or the operator may override any pre-set protocol to modify the perfusate manually.

In certain embodiments, the oxygen level of the reperfusate is directly modulated by changing the oxygen content of the fluid. In other embodiments, the oxygen levels reaching the tissue are modulated by altering the flow rate of the fluid, or by altering an rate of mixing of a supply of oxygenated and deoxygenated fluids. The deoxygenated fluid and/or the oxygenated fluid can be blood. In some embodiments, the oxygen levels are measured as a partial pressure of oxygen in the fluid. The oxygen levels can also be measured as an oxygen saturation or oxygen content of the perfusate.

In another embodiment of the invention, a measurement of local tissue conditions by the tissue condition monitor, which may be a sensor or probe, is transmitted to the reperfusion controller, which sets the desired starting oxygen level of the reperfusate produced by the reperfusate generator. The oxygen level of the reperfusate is adjusted by the controller in response to the condition of the ischemic tissue. The reperfusate is used to reperfuse the ischemic tissue. As the ischemic tissue recovers and the local tissue conditions change the reperfusion controller adjusts the desired reperfusate oxygen levels to control the therapy based on continued, ongoing tissue condition measurements. Such perfusate oxygen levels can be set using an algorithm or protocol that can be selected based upon the initial tissue condition or that may be manually controlled by the operator.

In another embodiment, the invention provides an apparatus for adaptive reperfusion that comprises a tissue condition monitor, a reperfusion controller operably connected to the monitor, and a reperfusate generator that is controlled by the reperfusion controller.

The tissue condition monitor can be one or more probe or sensor in any form that can be either inserted into the tissue being measured or can be extraneous to the tissue. The monitor can collect data from multiple probes or sensors and integrate the data to provide a signal to the reperfusion controller. In one exemplary embodiment, the condition of the ischemic tissue is measured using at least one oxygen probe or sensor that has been guided into the heart and inserted into the cardiac tissue. The cardiac tissue that the probe or sensor measure has typically been oxygen deprived for a period of time and is ischemic. The monitor measures the identified parameter, such as oxygen level of the tissue, and transmits a signal to the reperfusion controller. The device and method described herein allow the ability to set a reperfusion strategy based upon the actual condition of the tissue as reflected by the tissue condition monitor.

The reperfusion controller commands the reperfusion generator to generate reperfusate to the specified oxygen content. The controller processes the signals received from the tissue condition monitor to derive a measurement of a parameter, such as local oxygen levels, in the ischemic tissue. The controller compares the measured levels to a desired tissue parameter level, and commands the reperfusion generator to generate reperfusate with an oxygen content, flow rate or mixture rate that causes tissue parameter levels to change in a way to match the desired tissue parameter profile. Typically, the controller therefore includes a microprocessor to compare the levels and provide the appropriate commands.

The reperfusion controller may use tissue condition measurements as inputs to an algorithm. The reperfusion controller may be automatically or manually set in response to tissue conditions. In specific embodiments, the reperfusion controller is automatically set and is responsive to a predetermined algorithm. The reperfusion controller algorithm may be a closed loop control algorithm. The algorithm may implement a closed loop servo. The algorithm may utilize data parameters that can be changed by a user or by an external device. The algorithm may take into account the passage of time.

In certain embodiments, the reperfusion generator may be a venous blood oxygenation apparatus, such as a heart-lung machine, that can increase the oxygen levels in a fluid in response to a controller command. In other embodiments the reperfusion generator may be a deoxygenator that can reduce the oxygen content of an input fluid, such as arterial blood or previously oxygenated blood, to a level commanded by a controller. In another embodiment the reperfusion generator may be any device that can generate desired oxygen levels in a reperfusate in response to controller commands. In one exemplary embodiment of the invention, the reperfusion generator is an apparatus such as that disclosed in U.S. Pat. No. 7,455,812. In this embodiment, a mixed blood line can provide the reperfusate. The mixed blood line provides a mixture of both oxygenated and deoxygenated blood to the tissue. The mixed blood line allows for gradually increasing the oxygen tension of the perfusate without circulating venous blood through an oxygenator, which may limit the protective nature of venous blood.

In certain embodiments, the reperfusate is delivered to the ischemic tissue through a catheter. In some embodiments of the invention, the invention is used in a percutaneous procedure. In other embodiments, the reperfusate is delivered by tubing from the reperfusate generator to the ischemic tissue zone. The catheter or tubing may be connected to the ischemic tissue either percutaneously or through a transthoracic procedure. In certain embodiments, the reperfusion generator is further attached to an interventional catheter. In this embodiment, the reperfusate can be delivered to the ischemic tissue during a percutaneous coronary intervention (PCI) using a catheter that has been introduced into a coronary blood vessel. In this embodiment, the interventional catheter would be configured to provide the perfusate in a manner that would block the flow of unmodified blood to the region. Such a catheter can be configured with a proximal occluding member. A catheter can be configured to allow flow to only the infarct vessel (that which is being intervened upon). Alternatively, the catheter could be configured to be attached to a more global perfusion device, or, in one non-limiting example can be an aortic catheter that contained the proximal occluding member. Such catheters are described, for example, in U.S. Pat. No. 6,866,650 to HeartPort. In one embodiment the proximal occluding member is threaded through a central or more peripheral lumen of such a catheter. The catheter can be positioned using a percutaneous or transthoracic procedure to avoid exposure of the tissue to a perfusate with an undesirable composition or oxygen level. The tissue condition monitor can gather and then provide data to the reperfusion controller for the desired stating composition of the perfusate as well as providing ongoing data as recovery and reperfusion progress, thus determining the shape of the oxygen curve as a function of time.

BRIEF DESCRIPTION OF THE FIGURES

FIG. 5 is a schematic of the method of controlling the reperfusate oxygen levels.

DETAILED DESCRIPTION

Figure 1:
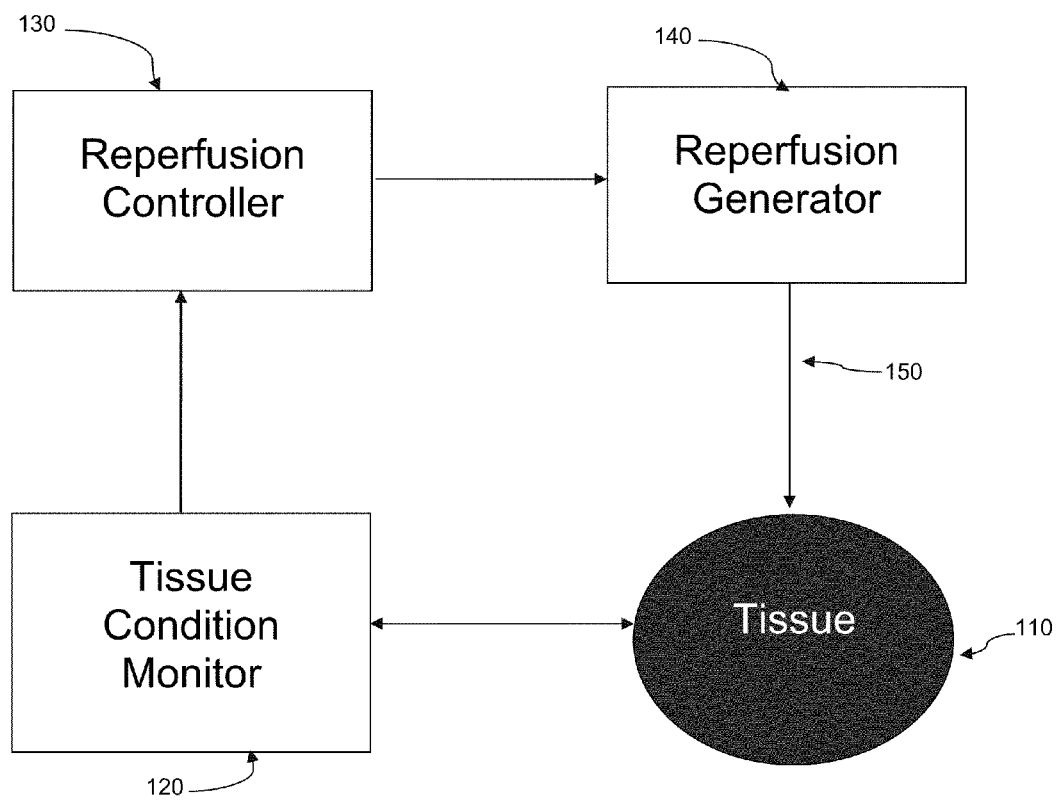
FIG. 1 is a schematic of the apparatus described herein.

The present invention is based on a recognition that reoxygenation of previously ischemic tissues should be modulated in response to local conditions and based, further, upon an appreciation that such conditions change dynamically during pharmacological and mechanical alterations of the circulatory system. The methods and apparatus described herein provide a tool that can respond to the local tissue environment of the ischemic heart by measuring both the antecedent and dynamically changing condition of the tissue affected by the existent ischemia and ongoing reperfusion; then controlling oxygen levels of the reperfusate as a function of time during re-introduction of oxygen. As recovery begins, it is intended that this apparatus and method allow ongoing adjustment of perfusate oxygen levels in response to the actual conditions of that ischemic tissue. This is in contrast to existing techniques that estimate or that simply ignore the tissue condition.

Indeed, under existing guidelines, many patients are misjudged to have either more or less severe antecedent ischemia based solely upon clinical parameters defined decades earlier rather than a precise measurement of tissue condition. Such a tissue condition monitor can be linked to a perfusate device that is operable and configured to deliver a "mixed blood line" perfusate that is modifiable with respect to oxygen levels as a function of time. In some embodiments, the device to generate the perfusate is one such as that described in U.S. Pat. No. 7,455,812. Such a mixed blood line or other configuration for controlling oxygen levels may be connected to an interventional catheter system or may be configured to be a part of a systemic cardiopulmonary bypass circuit with a separate cardioplegia or coronary perfusion circuit.

In many clinical cases treatment is delayed or denied in the acute presentation because of potential for tissue damage that may occur upon the reintroduction of oxygen in circumstances in which antecedent ischemia is particularly protracted or severe. Treatment may also be initiated inappropriately based upon clinical parameters that underestimate the severity or duration of the antecedent syndrome. In such circumstances, extensive reperfusion damage may occur that was not anticipated based upon an erroneous judgment of tissue condition. The present invention is particularly useful in those patients with the most protracted or severe pre-existent ischemia because the apparatus can mitigate injury to such tissue upon acute reperfusion. It should be pointed out that the antecedent severity of the tissue ischemia may not be accurately reflected by the appearance of the patient or any externally measurable clinical parameter as these may not be congruous.

The present invention addresses the acute tissue condition, allowing a feedback loop that is configured to provide a real-time guide to the interventional strategy. The invention allows the clinician to address all patient groups whether ischemia is protracted and/or severe or abbreviated and/or mild without being misled by the clinical appearance of the patient on either end of the clinical spectrum.

Accordingly, in one embodiment, the invention provides a method of treating an ischemic event in a host comprising measuring local tissue conditions in a host tissue and modulating oxygen levels of a reperfusate being delivered to the host based on the measurement. The measurement of tissue (110) condition is accomplished using a tissue condition monitor (120). The tissue condition monitor is linked, directly or indirectly, to a reperfusion controller (130) that controls the oxygen content of the reperfusate (150) generated by a reperfusion generator (140). The controller modulates the reperfusate to deliver differing levels of oxygenated fluid to the ischemic tissue.

In certain embodiments, the oxygen level of the reperfusate is directly modulated by changing the oxygen content of the fluid. In other embodiments, the oxygen levels reaching the tissue are modulated by altering the flow rate of the fluid, or by altering a mixture rate of oxygenated and deoxygenated fluids.

Clinical Scenarios:

The methods and apparatus of the present invention can be useful in a variety of clinical scenarios.

Acute percutaneous coronary intervention (acute PCI) with or without intra-aortic balloon or cardiopulmonary support during evolving ischemia can be facilitated by the method and apparatus described herein. An assessment of the ischemic conditions with the tissue condition monitor allows an appropriate starting point for initial reperfusate oxygen level. In certain instances, the patient is administered a pharmaceutical agent, for example, vasoactive or beta-blocking pharmaceutical agents. Intra-aortic balloon support is widely appreciated to support the coronary and systemic circulations by enhancing perfusion in both and, as such, affecting the supply side of the ischemia balance and by enhancing tissue oxygen delivery (systemic or coronary). This explains why such support is often used in patients with cardiogenic shock prior to, or in lieu of, other forms of mechanical circulatory support (such as cardiopulmonary bypass, ECMO or ventricular assist or artificial heart pump support). Such support with a balloon pump could alter the starting point of perfusate oxygen level.

The present invention can also be useful in coronary bypass grafting, either on- or off-pump and with or without balloon support. In emergency coronary bypass operations, whether done "on pump" or "off pump", little appreciation exists for any assessment of the antecedent condition of the tissue or the manner in which the condition of the tissue may be altered by intra-aortic balloon support, the initiation of cardiopulmonary bypass or even the induction of general anesthesia. The present invention allows for a very precise, surgical accounting of tissue condition and could be expected to enhance the practice by allowing for a manipulation of perfusate oxygen tension, saturation or content in response to real-time tissue conditions. The altered oxygen content fluid can be delivered to the tissue during or via vein graft bypass or catheter based perfusion to the infarct (or other) artery. Vein graft perfusion after completion of a coronary anastomosis can be facilitated by a blood pump as described in the present invention. Such a perfusion pump can be free-standing in "off-pump" cases or integrated into a heart-lung machine in "on-pump" cases as described in U.S. Pat. No. 7,455,812 and configured to receive a mixed blood supply that carefully controls oxygen partial pressure, saturation or content. In certain embodiments, the intervention is thus a vein graft intervention can be facilitated by the present invention after careful assessment of the condition of the tissue is presented to the operator in the operating room. In addition, appropriate reperfusion control may be useful in non-cardiac ischemia, such as during limb reperfusion or brain injuries including stroke and traumatic brain injury (TBI).

Tissue Condition Monitor

It is well established that patients can adapt to levels of chronic or intermittent coronary ischemia to differing degrees. Even varying intensity of acute ischemia can be remarkably well tolerated, particularly if they are not protracted events. Different patients who possess identical coronary disease anatomy (including total occlusions) may have adapted to this anatomy as it progressed over a chronic timeframe. In another example, coronary anatomy in the same patient that does not necessarily change may take on different significance in the setting of an acute coronary syndrome. As such, the anatomy of the epicardial vessels tells only one part of the story. The overall clinical condition of the patient tells another. For that reason, "gross" or "macro" measurements (i.e. angiographic appearance) may guide the clinician or provide a road map of where to inflate a balloon or where to place a stent, however they do not accurately reflect the condition of the tissue supplied by that artery at any given time.

In the setting of the treatment of acute evolving coronary ischemia, the present invention allows the operator to respond to actual tissue conditions rather than the patient's clinical appearance, which may be inaccurate. The best previously available clinical constructs for the guidance of interventional treatment are based upon data from interventional studies of another era and the entire premise upon which these guidelines are based allows no assessment of the tissue condition. While timely reperfusion or opening of the "culprit" vessel has been shown to be useful in saving lives and improving outcomes, damage to the heart during reperfusion therapy adds to the injury.

Therapeutic, acute percutaneous balloon catheter intervention with or without stenting with advanced anti-platelet and other anticoagulation or urgent coronary bypass surgery are still the only known and best therapies available to establish reperfusion of the ischemic heart. It is clear that the timing of such intervention has been based upon inexact criteria as acute mortality rates remain high in subsets of patients (e.g. cardiogenic shock) and therapy is not offered to the majority of patients during the acute event because of the fear of poor clinical outcomes that can accompany reperfusion or other additional cardiac injury during the re-establishment of flow into the ischemic tissue.

Although the clinical appearance of a given patient and the responses to reduced oxygen availability in acute or chronic situations vary greatly from patient to patient (based upon reserve, adaptation, chronicity of atheromatous growth and development of collateral flow), cells subjected to protracted and uncompensated ischemia react in a remarkably similar and in a highly evolved manner to attempt to adapt to ischemic conditions. The cellular changes that proceed during these events ultimately lead to disturbances from which the cell may or may not recover. The cellular recovery depends largely upon what happens during the phase in which oxygen and other nutrients are reintroduced During the reestablishment of blood flow and reintroduction of molecular oxygen, the relationship between the availability of oxygen to the tissue, the demand for oxygen in the tissue and the precise manner in which oxygen is reintroduced and the pre-existing cellular conditions all govern whether recovery or further tissue injury occurs. In accordance with this discussion of tissue condition monitors, it is, therefore, important to have a tool to determine the presence, absence and severity of the cellular ischemic conditions at the time reperfusion therapy is undertaken.

The purpose of the tissue sensor in ongoing acute coronary ischemia is to accurately determine the severity of the cellular alterations present. By measuring tissue conditions during therapy rather than looking at the outward appearance of the patient and the EKG as a "clinical" presentation, life saving and "tissue-saving" therapy can be offered to a broader range of affected patients. For illustrative example; while it is widely accepted that the clinical presentation of cardiogenic shock requires more than 40% of functioning myocardium to be poorly contractile (hypokinetic or akinetic), not all of that tissue is necessarily acutely ischemic nor irreversibly damaged. While it is widely accepted that such a patient undergo immediate percutaneous or surgical reperfusion therapy, the present invention allows for an accurate assessment of the affected tissue at the cellular level. This can allow the careful tailoring of therapy to each individual patient and each of the affected myocardial areas to guide oxygen partial pressure and the timing curve of therapy as compared to the "one-size-fits-all" approach of previous decades.

In certain clinical instances, the demand of the heart tissue for oxygen may be reduced. For example, in cases in which mechanical support is used to unload the heart (either with a balloon pump or cardiopulmonary bypass) the reduction in demand for available oxygen must be accounted for in the resuscitation phase of treatment. When the heart is doing no pressure-volume work, the demand of the heart tissue for oxygen and nutrients is recognized to be about 50% below basal conditions. In instances in which the heart is stopped using cardioplegia, the demand is lowered to about one tenth normal. In contrast, in an awake patient without mechanical support the heart may be working at much higher than basal conditions exacerbating both global and regional ischemic conditions and setting the stage at the cellular level for increasing the likelihood that serious reperfusion damage will result upon either reintroduction of molecular oxygen by reestablishing flow or by the elimination of ischemic conditions. It should be pointed out for the purpose of clarity and relevance to the present invention that these two scenarios may be effected in various ways and by alterations in both supply of and demand for oxygen.

The tissue condition monitor can comprise a sensor embedded in the myocardium to give tissue specific information. However, the monitor may also lie within the extensive system of coronary venous drainage giving information regarding regional oxygen extraction. In certain embodiments, the monitor is not a sensor, but is a molecular biomarker (probe) that is infused and taken up by the machinery of the cells to provide a particular readout that can be measured by external sensors such as visual, electromagnetic or nuclear imaging. The tissue condition monitor may also be a non-invasive modality such as MRI, PET or ultrasound.

The tissue condition monitor can comprise one or more sensors in any form that can be either inserted into the tissue being measured or can be extraneous to the tissue. The tissue condition sensor can comprise a signal processing means to process the raw signals being generated by a tissue sensor or sensors. The tissue condition sensor may be guided to the tissue of interest with the aid of an imaging means. Such imaging modalities include ultrasound, fluoroscopy, PET and MRI.

In one embodiment, a simple echocardiographic assessment of a wall motion abnormality and regional EKG changes would allow the positioning of a tissue sensor using fluoroscopy in a "culprit" coronary artery, in the area of venous effluent drainage of that region or in the same region that appears ischemic based upon the assessed changes seen by myocardial contrast echocardiography. Other techniques using information on the tissue that is affected to position the sensors include positron tomography (PET) scans or cardiac magnetic resonance (MRI). Nuclear medicine scanning for the uptake of thallium or other like molecules can define clinical ischemia as well.

Typically, the more intense and protracted the ischemia; the higher the likelihood that the tissue is overwhelmed by oxidative stress and reactive oxygen intermediates are formed rather than channeling molecular oxygen into oxidative phosphorylation and cellular recovery. These oxygen free-radicals can cause lipid bilayer peroxidation and the initiation of violent calcium oscillations that lead to contracture and stunned myocardium at one end of the spectrum to calcium overload and cell death at the other. Further, such oxidative stress in those circumstances has been linked to the upregulated activity of inflammatory mediators, the expression of cytokines, adhesion molecules and, possibly, the expression of transplant rejection-related, major histocompatibility complex (MHC) antigens.

Embedded tissue sensors may measure, as non-limiting examples, tissue pH, $PO_2$, $pCO_2$, temperature, ion concentrations including potassium, sodium or calcium concentrations in the extracellular environment, cellular membrane depolarization, hyperpolarization or resting membrane potential, cyclin dependent kinases (CDK), B-type natriuretic peptide (BNP), tumor necrosis factor $\alpha$ (TNF-$\alpha$), creatine phosphokinase, lipid peroxidation byproducts such as aliphatic aldehydes including malonic dialdehyde, PMN elastase, NFkB, Na—H Exchange pump activity. U.S. Pat. Nos. 5,813,403, 6,564,088, and 6,766,188, describe a method and device for measuring tissue pH via near infrared spectroscopy (NIRS). NIRS technology allows the simultaneous measurement of tissue saturation of oxygen, carbon dioxide as well as pH.

The monitor can collect data from multiple sensors and integrate the data to provide an integrated signal or signals to the reperfusion controller. In one exemplary embodiment, the condition of the ischemic tissue is measured using at least one oxygen sensor that has been guided into the left ventricle of the heart and inserted into cardiac tissue. A non-limiting example of such a monitor would be one that is advanced into the LV chamber on a catheter-based carrier and then deployed under guidance of a trans-esophageal echo probe to engage the tissue to a certain depth; usually as deep as or deeper than the sub-endocardial layers. The cardiac tissue that the sensor is inserted into has typically been oxygen deprived for a period of time and is ischemic. The monitor measures the identified parameter, such as oxygen level of the tissue, and transmits a signal to the reperfusion controller. Another illustrative example of tissue examination under such conditions is the use of myocardial contrast echocardiography, which could also be applied to determine acutely affected tissue to allow guidance of a sensor into position for a more accurate probing of tissue condition. Other techniques to locate sensors include positron tomography (PET) scans or cardiac magnetic resonance (MRI). These illustrative examples are intended to be non-limiting.

Figure 2:
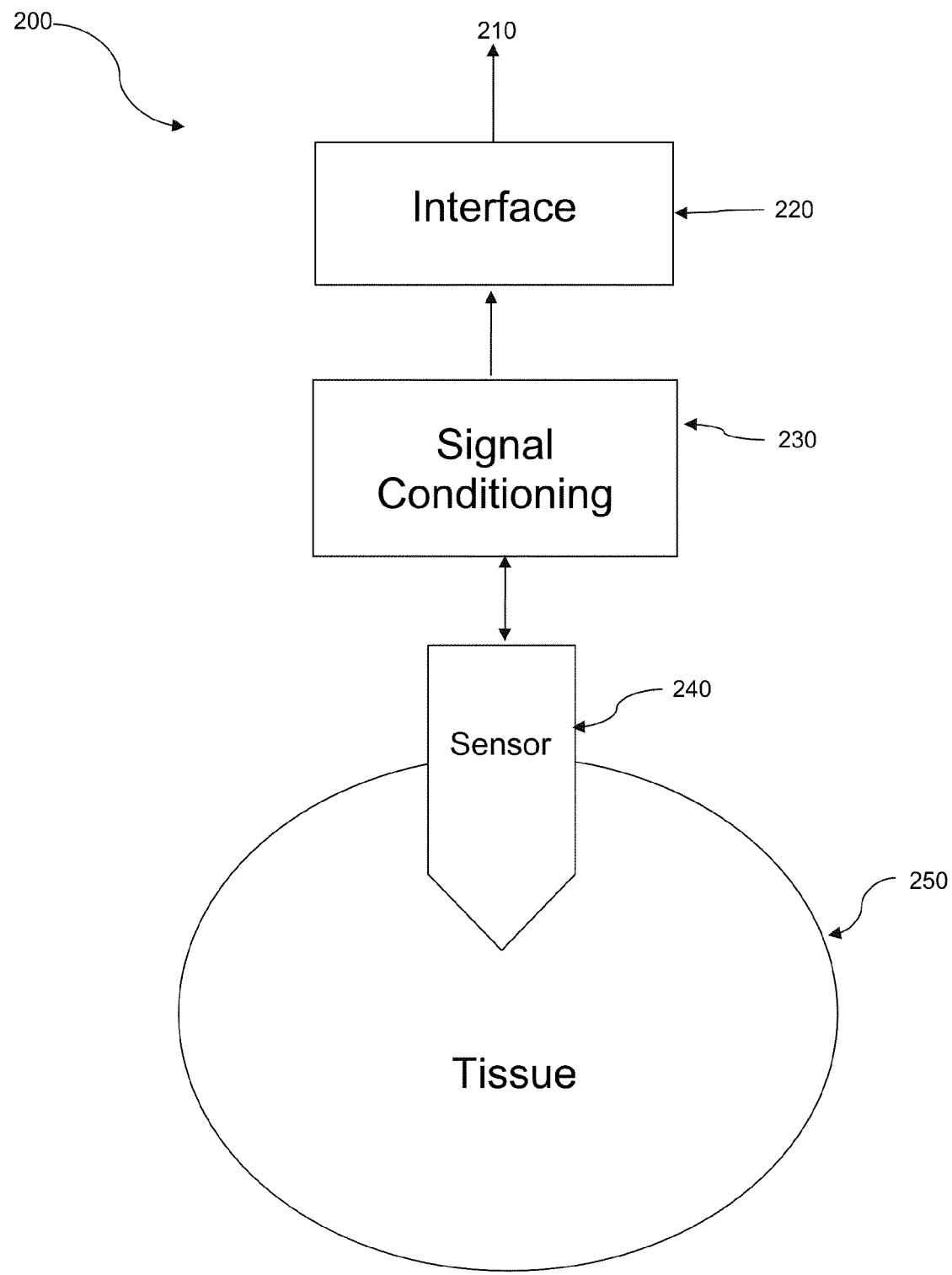
FIG. 2 is a schematic of the tissue condition monitor.
Figure 3:
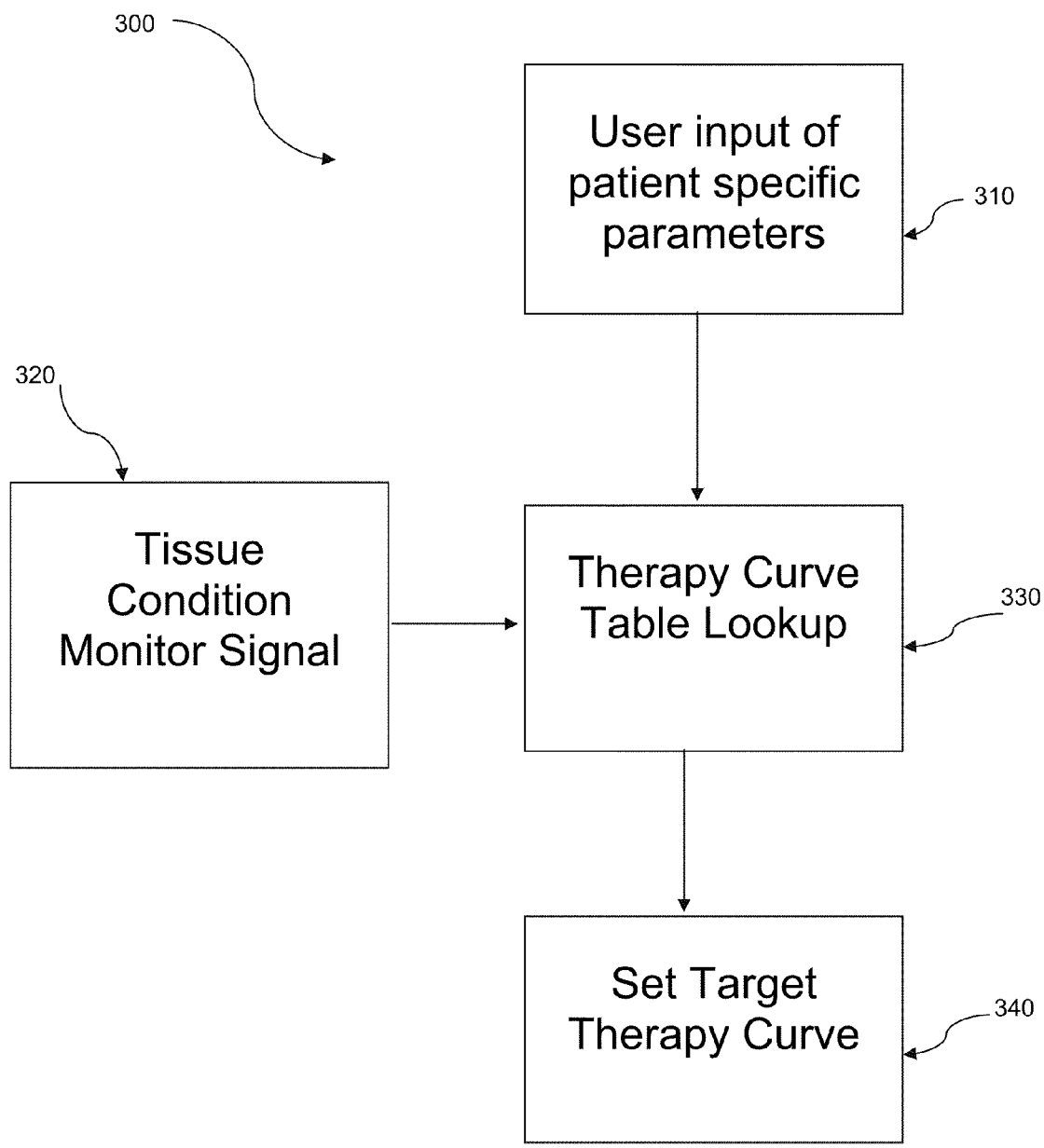
FIG. 3 is a schematic of the method of target therapy curve selection.

In one embodiment shown in FIG. 2 (200), a tissue sensor (240) is inserted in the ischemic cardiac tissue (250) and is used to sense a tissue parameter, such as $pO_2$. The raw signal from the tissue sensor is processed by the signal conditioning circuit (230) to generate a value representative of the parameter being measured. This value is processed by the interface (220) that takes the output of the signal conditioning (230) block and configures it in a signal (210) appropriate for transmission to the reperfusion controller.

The condition of the ischemic tissue may also be measured by a non-invasive means. This measurement may measure parameters relating to the local chemistry or physiology of the tissue or may measure morphologic parameters. Current echocardiographic and EKG changes can allow determination of wall motion abnormality and a region that appears ischemic based upon the changes seen on a 12-lead EKG. Nuclear medicine scanning for the uptake of thallium or PET or SPECT imaging using radiolabeled RBC's can all define cellular metabolism or degree of perfusion as well. The tissue condition measurement may reflect functional parameters such as motion, contractility or cellular respiration.

In some embodiments the measurement of the tissue condition is made using at least one tissue sensor. The tissue sensor may measure pO2 in the tissue or may measure oxygen saturation of hemoglobin within red blood cells in circulating blood in some blood vessel that can provide information on oxygen extraction or cellular metabolism. The tissue sensor may also measure any other parameter that can be linked clinically and/or experimentally to severity of ischemia that may be used by the reperfusion controller to determine appropriate perfusate oxygen tension or composition. The tissue condition monitor may also measure more than one parameter. In embodiments where more than one parameter is measured, a single tissue sensor may be used to make the measurement or a plurality of sensors may be employed. In some embodiments the condition of the ischemic tissue is sensed by a sensor positioned in the ischemic tissue itself. In other embodiments the condition of the ischemic tissue is sensed by a sensor remote from the ischemic tissue itself. In some other embodiments; a plurality of sensors may be deployed under some guidance to the operator and positioned in both ischemic and non-ischemic areas of the heart. One non-limiting example of such a preferred embodiment would be that the processor would rapidly compare the tissue parameter of the ischemic to the non-ischemic area and set the controller to perfuse the tissue in a pre-set manner. Such preset manner could be over-ridden manually if the operator chooses.

In some embodiments the tissue condition monitor includes a sensor guided to the ischemic area using visual guidance from a fluoroscope, myocardial contrast echocardiograph, and ultrasound imaging system, MRI scanner, PET scanner or other imaging modality. This imaging modality may be used to detect areas of compromised cardiac function (e.g. abnormal heart wall motion) indicating ischemic tissue. The imaging modality may also be used to help guide the tissue sensor itself for positioning.

Sensors that can assess markers of acute ischemia, the consequences of reperfusion injury or other processes that occur during acute coronary events may be used in the tissue condition monitor. In certain embodiments, the condition of the ischemic tissue may be inferred from measurements made not in the tissue itself. In one embodiment, a parameter or parameters of blood distal to the ischemic tissue is/are measured. In the event that the blood distal to the ischemic tissue is mixed with blood from other areas, the reperfusion controller may make calculations to infer the contribution to the measured parameter of the blood from the area of interest.

The blood measured may be in the coronary sinus, measured with a fluid sensor, a sensor with oxymetric capability or some other means by which to determine oxygen extraction as a surrogate for ischemic conditions. It may be determined that the best scenario to determine the output of the controller is to measure a combination of such parameters and then to evaluate a ratio or some other relationship of one parameter to the other to determine reperfusion controller output.

The sensor may be attached to a support structure such as a stent, guidewire, or catheter. In a further embodiment, a catheter is disclosed that extracts samples to a sensor outside the body for monitoring a substance or property of the patient sample.

In certain embodiments, the sensors specifically assess the saturation of oxygen or the $pO_2$ in coronary sinus effluent. Further, intra-coronary sinus pH changes may be highly related to the severity of the ischemic conditions. In addition, factors indicative of tissue condition that may be monitored in the coronary sinus include leukocyte elastase, tumor necrosis factor (TNF), basic FGF, von Willbrand factor (as a surrogate for P-selectin), p-selectin, nitrate and markers that may represent bi-products of lipid peroxidation (like malondialdehyde) or other cytokines. This list is intended to be illustrative rather than limiting. Such coronary sinus sensors or probes that now exist or that might be invented in the future can be used to assess the progress, safety and subsequent composition of the ongoing reperfusion therapy.

In certain embodiments, tissue $CO_2$ can also be measured, for example as described in U.S. Pat. No. 6,055,447, which describes a tissue $CO_2$ sensor. Sensors can be of any type, but include fiber optic sensors, nanoparticle sensors, and even biologic sensors. US Patent Publication No. 20060079740 to Silver, et al. provides a sensor for implantation within a blood vessel that can detect nitric oxide or a nitric oxide metabolite, substances such as glutamate, aspartate, arginine, citrulline, acetylcholine, calcium, potassium, or dopamine.

Reperfusion Controller

The reperfusion controller commands the reperfusion generator to generate reperfusate to a specified oxygen content. The controller processes the signals received from the tissue condition monitor to derive a measurement of a parameter, such as local oxygen levels, in the ischemic tissue. The controller compares the measured levels to a desired tissue parameter level, and commands the reperfusion generator to generate reperfusate with an oxygen content, flow rate or mixture rate that causes tissue parameter levels to change in a way to match the desired tissue parameter profile. Typically, the controller therefore includes a microprocessor or other logic to compare the levels and provide the appropriate commands.

In some embodiments, the reperfusion controller receives sensor input that has already been processed to provide a final sensor reading. In other embodiments, the reperfusion controller processes raw sensor signals to derive a sensor reading. The reperfusion controller may take one or more sensor signals as inputs. The controller may take inputs from modalities that generate information relating to the condition of the ischemic tissue. The reperfusion controller may also take input from a user or from an external device. This input may be information related to the condition of the patient. This input may also be treatment direction from a user. In certain embodiments, the reperfusion controller automatically controls the reperfusate oxygen level based on a preset algorithm. In other embodiments, the reperfusion controller controls the reperfusate oxygen level based on a manual input from an operator.

Control

The present invention addresses the actual condition of the affected tissue and microcirculation. The essence of the invention relates to using real-time feedback to identify the underlying condition of the tissue which relates to its potential response to therapy, rather than estimating tissue conditions based upon clinical appearance, EKG changes, elevated serum biomarkers or other factors that are either global or delayed. The therapy described herein addresses the condition of the underlying tissue to provide a real-time feedback that is deployable in the ER, the ICU or the cath lab that guides reperfusion therapy. The technology takes into account factors affecting oxygen supply (i.e. the narrowed/occluded arteries, blood hemoglobin levels, evidence of endothelial activation, etc.) and demand (i.e. how hard the heart is working, ventricular wall stress, afterload, preload, heart rate, etc.). To date, very little control over anything other than the timing of intervention has been used and accurate or reliable resuscitation of threatened tissue has not been possible. Even less information regarding the success or failure of reperfusion in real time at the cellular, microcirculatory or molecular levels has been available.

The condition monitored can be of individual cells or a reflection of the condition of the micro-vascular environment (including endothelial activation, platelet adherence or release into the microcirculation of markers of injury) and provide a real time reflection of metabolic processes, microcirculatory failure or cellular injury and could be correlated with the appropriate perfusate $pO_2$.

The reperfusion controller may use tissue condition measurements as inputs to an algorithm. The controller may also use inputs not related to the condition of the ischemic tissue as inputs to an algorithm. Such inputs may be information regarding the patient, time since the beginning of the event, parameters that were measured before intervention such as muscle wall abnormalities, or other information that can be inputs to an algorithm. Such inputs may include input from a user. The output of the reperfusion controller may control information for a reperfusate generator.

The reperfusion controller algorithm may be a closed loop control algorithm. The algorithm may implement a closed loop servo. The algorithm may utilize data parameters that can be changed by a user or by an external device. The algorithm may take into account the passage of time.

The algorithm for the reperfusion controller may be fixed or may be changed from time to time. In the case where it is changed, it may be changed to another algorithm previously stored in the controller or it may be downloaded from a source external to the controller. The algorithm may be changed by changing the steps it executes or by changing how the steps are executed.

In one embodiment initial user-input parameters are used to guide the reperfusion therapy. Such parameters may include patient-specific information such as age, sex, and time since ischemic event. This information is input (310) to the reperfusion controller algorithm (300) along with information from the tissue condition monitor (320). In one embodiment, this information is used to select a target therapy curve (340) from a table (330) of possible curves. The target therapy curve defines the time-variable target for the tissue condition monitor signal that the reperfusion control should attempt to achieve. The target therapy curve may include associated information such as how changes in reperfusate oxygen will affect the measured parameter (negative or positive correlation) and information as to expected sensitivity of the measured parameters to reperfusate changes and allowed reperfusate change slew rates along with total length of therapy. For example, a target therapy curve for $pO_2$ would include information that an increase is reperfusate oxygen content would be expected to increase measured tissue $pO_2$ or some other parameter indicating both recovery of cellular and mitochondrial function (including restoration of oxidative phosphorylation and recovery of trans-membrane polarization toward normal) and the avoidance of producing indicators of, for example, lipid peroxidation.

Figure 4:
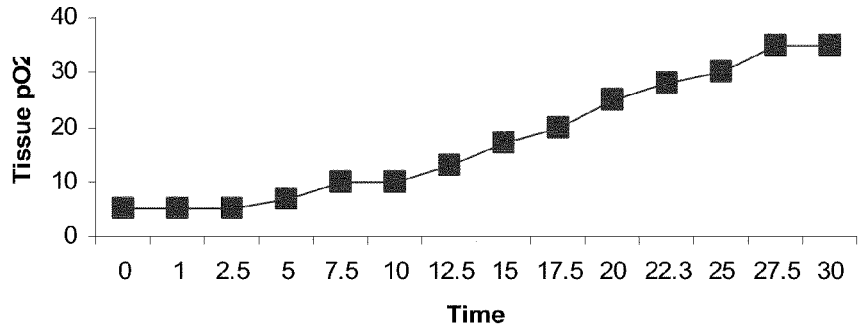
FIG. 4 is drawing of exemplary target therapy curves.
Figure 4:
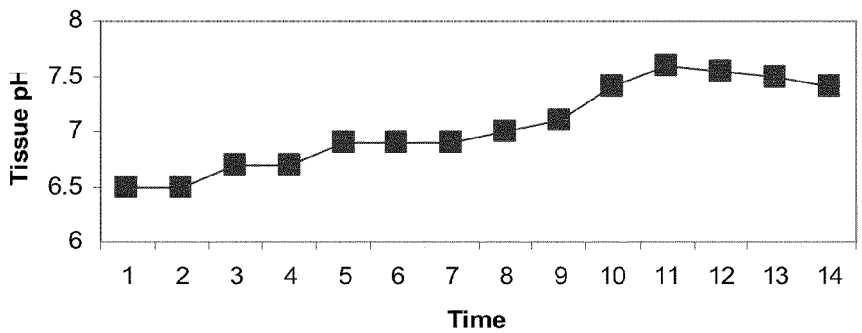
Figure 4:
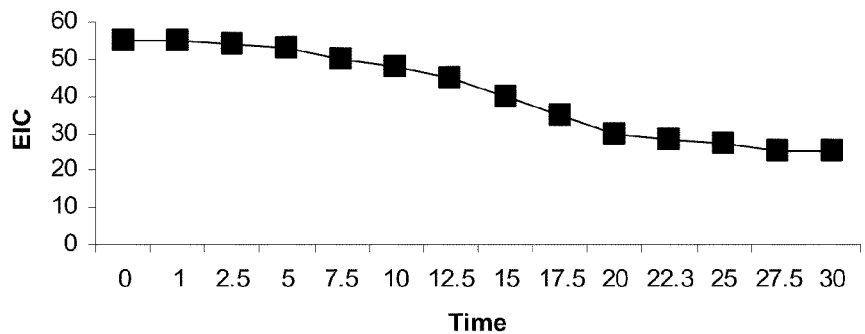

FIG. 4 shows non-limiting representative examples of three target therapy curves. In one embodiment the target therapy curve is based on measurement of $pO_2$ (410). In another embodiment the curve is based on measurement of pH (420). In a third embodiment, the curve is based on measurement of elastase $\alpha_1$-protease inhibitor complexes (EIC) (430). In yet another embodiment, the curve is based on measurement of tumor necrosis factor (TNF). In yet another embodiment, the curve is based on measurement of basic FGF. In yet another embodiment, the curve is based on measurement of von Willebrand factor or p-selectin. In yet another embodiment, the curve is based on measurement of nitrate. In yet another embodiment, the curve is based on measurement of malondialdhyde. In other embodiments, this curve may actually be a multidimensional "surface" based on the measurement of a plurality of tissue parameters.

The reperfusion controller (130) controls the reperfusion generator (140) in an attempt to cause the measured tissue parameter to track the selected target therapy curve over time. In one embodiment, an algorithm (500) is used to generate the signal to the reperfusion generator. At the beginning of the therapy time t is set to zero (510). The starting reperfusate $pO_2$ (r_pO2) is retrieved from a table associated with the previously selected target therapy curve (520). Then the reperfusate generator is commanded to produce reperfusate having properties r_pO2 (530). A time interval delta-t is allowed to pass (540) and then a measured tissue parameter TPmeas is retrieved from the tissue condition monitor (550). TPmeas is compared to the desired parameter level as specified in the selected target therapy curve for that time TPcurve(t) (560). If the measured parameter is the same as the desired level, the loop continues without changing r_pO2. If there is a difference, a delta_r_pO2 is computed and added to the current r_pO2 to generate a new r_pO2 (570) and loop continues with step 530 with a new pO2 command to the reperfusate generator. Delta_r_pO2 may be computed by techniques used in closed loop control algorithms. In one embodiment an equation such as delta_r_pO2=(TPcurve(t)−TPmeas)*(sensitivity) could used. In certain cases, the "sensitivity" can be a negative number, i.e. the correlation coefficient is negative.

In certain embodiments, the reperfusion parameters are designed to provide normalization of perfusion to tissue within one hour of initiation. In other embodiments, they are designed to provide normalization in less than one hour, such as in 45, 30 or less than 30 minutes such as, for example, 25, 20, 15, 10 or 5 minutes after initiation of therapy. In some embodiments, additional measurements are conducted on tissue conditions after therapy to identify potential injuries.

Reperfusion Generator

In certain embodiments, the reperfusion generator may be a venous blood oxygenation apparatus that can exploit the protective nature of venous blood perfusion during acute reperfusion of ischemic tissue, such as a heart-lung machine, and that can increase the oxygen levels in a fluid in response to a controller command. In such an embodiment it is recognized that the protective nature of venous blood may relate to the lower oxygen tension present or may relate to a different component of venous blood. In other embodiments the reperfusion generator may a deoxygenator that can reduce the oxygen content of an input fluid, such as arterial blood or previously oxygenated blood, to a level commanded by a controller. In another embodiment the reperfusion generator may be any device that can generate desired oxygen levels in a reperfusate in response to controller commands. The reperfusion generator can also be any device that can modify the oxygen level delivered to the tissue, i.e. by modifying the flow rate, in response to controller commands.

In one exemplary embodiment of the invention, the reperfusion generator is an apparatus such as that disclosed in U.S. Pat. No. 7,455,812. In this embodiment, the mixed blood line can provide the reperfusate. The mixed blood line provides a mixture of both oxygenated and deoxygenated blood to the tissue and exploits the protective nature of venous blood for as long as the clinical situation warrants that is based upon the precise condition of the tissue.

In certain embodiments, the reperfusate at a point in the process includes a high level of oxygen, such as through an oxygen supersaturated fluid. However, the high level of oxygen is typically not delivered until after the tissue condition monitor provides measurements that indicate that the tissue has recovered sufficiently to reduce risk of reperfusion/reoxygenation injury. This recovery might be signaled in a number of ways or be reflected by the tissue condition monitor sensor or probe, but, as a non-limiting example, may be signaled by a normalization of pH.

In certain instances, the reperfusate undergoes further processing such as by inserting leukocyte filters into the delivery circuit and by gradually adjusting the admixture of venous and arterial blood in a carefully controlled reoxygenation strategy.

In some embodiments, the reperfusion generator regulates the rate at which blood is delivered to the tissue. For example, the reperfusion generator can regulate the inflation of a balloon in the vessel. In other embodiments blood may be supplied in a compartmentalized fashion by engaging a proximal occluding member in both the artery upon which the intervention is being performed and the other arteries. As described previously, the tissue within the myocardium may be affected by ischemia along a spectrum of severity and in areas other than that supplied by the "infarct" artery. As such, it is desirable to be able to control, in a compartmentalized way, the perfusate to both the acute "infarct artery" and the other arteries that may supply tissue that is affected by reduced collateral flow. In one embodiment, the catheter may be a central aortic catheter that has a large occluding member but that allows for the positioning of more than one separate catheter that each perfuses a different artery differently. In certain of these embodiments, the central lumen of the central aortic catheter can also be used to compartmentalize perfusion for global coronary perfusion while, simultaneously, a second and a third catheter inserted via another lumen (central or peripherally located) can be the interventional stent deploying catheter and a separate catheter with another downstream occluding member to control individual artery perfusion. In such an embodiment the elaborate catheter system described would be connected to the reperfusion generator described and, likely, a second perfusion device that was also adjustable with regard to oxygen partial pressure and various other parameters.

The reperfusate may be blood, a non-blood fluid or a mixture of the two. In certain embodiments, the reperfusion generator provides distinct reperfusates to the cardiac tissue and to non-cardiac tissue such as the brain. The reperfusates can include one that addresses the cardiac tissue appropriately and that perfuses specific coronary arteries (or multiple arteries) during PCI or surgery and is controlled by the controller, and another that allows for adequate oxygen delivery to the brain separate from the controller. Unless systemic oxygen tension is extremely low, as in cyanotic conditions or in cases where there is significant concomitant pulmonary disease or shock, separate perfusates allow the coronary perfusates to "match" the usually far lower $pO_2$ of the ischemic cardiac tissue based upon a real-time assessments.

Delivery

In certain embodiments, the reperfusate is delivered to the ischemic tissue through a catheter. In other embodiments, the reperfusate is delivered by tubing from the reperfusate generator to the ischemic tissue zone. The catheter or tubing may be connected to the ischemic tissue either percutaneously or through a trans-thoracic procedure or, in other embodiments, through both catheters, perfusion lines that are attached to the generator or via bypass grafts that are constructed via a trans-thoracic procedure. In certain embodiments, the reperfusion generator is further attached to an interventional catheter or may be connected simultaneously via several catheters in combination with another perfusion device (such a heart-lung machine).

In one embodiment, the reperfusate can be delivered to the ischemic tissue during a percutaneous coronary intervention (PCI) using a catheter that has been introduced into a coronary blood vessel. In certain embodiments, the reperfusion generator is attached to a vein graft or other surgically constructed conduit that has been surgically connected to the tissue via an anastomosis one or more blocked arteries. In certain other embodiments a combination of vein grafts perfused via a branched perfusion device can be connected to the reperfusion generator or a separate perfusion device (such as a heart-lung machine) while simultaneously a PCI catheter may also be providing controlled reperfusate to the "infarct" artery.

In some embodiments of the invention, the invention is used in a percutaneous procedure. In other embodiments, the invention is used during a transthoracic procedure. In particular embodiments of the invention, the host or subject to which the method and system is applied is a human who might be undergoing a "hybrid" percutaneous and trans-thoracic procedure. In specific embodiments, the host is a human who is in need of prevention of reoxygenation injury. In certain embodiments, the subject is a human patient with cardiovascular disease. In certain other embodiments, the subject is a human patient undergoing a transthoracic procedure. The procedure and apparatus can be used in a subject undergoing surgery after a cerebral infarct and concomitant ischemia, for example after a stroke. In addition, the patient can be undergoing intervention for an ischemic event in a limb. In cases in which the ischemic tissue is not cardiac tissue, the tissue sensors are placed in and measure the ischemic tissue, whether that is cardiac or not.

The methods and apparatus of the invention can be useful in the clinical arena of either cardiac surgery or interventional cardiology. They can be applied in acute percutaneous coronary intervention or urgent bypass surgery, but as discussed above, are also applicable in evolving "hybrid" treatments which may combine both PCI and surgical interventions. In some embodiments, it is intended to provide treatment for acute myocardial infarction with ST segment elevation. In certain embodiments, it is useful in treatment of "acute coronary syndrome" (ACS), which includes unstable angina and non-ST segment elevation myocardial infarction in which different areas of the heart may experience serious but variable degrees of ischemia along a spectrum of severity, which can be assessed properly by the tissue condition monitors to construct or prescribe an appropriate reperfusion strategy.

Typically, ACS occurs when an unstable plaque (potentially due to plaque rupture) leads to an acute and localized thrombosis in an area of stenosis or narrowing of a blood vessel, leading to ischemic regions in the tissue but which may also cause a reduction in collateral flow that has developed over time to other regions that results in ischemia that is not readily apparent.

The resultant infarction (the totality of tissue injury) occurs by a variety of mechanisms that relate to both the initial event and the manner in which flow is reestablished and oxygen is reintroduced. The initial ischemic insult sets the stage for cell death because of a protracted lack of oxygen that renders the cells unrecoverable as well as because of additional injury that occurs upon reoxygenation. This type of injury (reperfusion/reoxygenation) may relate to oxygen radical injury, microvascular failure and so-called "no-reflow", enhanced inflammation and leukocyte adherence (which goes hand-in-hand with oxygen radical formation), cardiomyocyte contracture via calcium overload and paralysis, platelet thrombin aggregation upon activated endothelial cells, among other mechanisms.

It will be apparent to one of skill in the art that the embodiments provided are merely exemplary, and that the invention should not be so limited. Accordingly, those of skill in the art will recognize various alternative designs and embodiments for practicing the invention. Those of skill in the art will also recognize its potential for use in both clinical and animal research to define alternatives and the most appropriate reperfusion curves that may vary as a function of time in differing situations.

The invention claimed is:

1. An apparatus for adaptive reperfusion that comprises a tissue condition monitor wherein the tissue condition monitor measures a measured tissue parameter associated with an ischemic tissue within a human body, a reperfusion controller operably connected to the tissue condition monitor and receiving input from the tissue condition monitor as to the measured tissue parameter of the ischemic tissue, and a reperfusate generator that is controlled by the reperfusion controller to create a reperfusate, the reperfusate controller comprising a processor and instructions for executing on the processor, wherein the instructions include at least one target therapy curve from which a target therapy curve can be selected and the at least one target therapy curve has at least one tissue reperfusion parameter that changes over time, and wherein the tissue condition monitor provides feedback to the reperfusion controller as to the measured tissue parameter to control the reperfusion generator to cause the measured tissue parameter associated with the at least one tissue reperfusion parameter to adjust the reperfusate so that the measured tissue parameter attempts to track the selected therapy curve as to the at least one tissue reperfusion parameter.

2. The apparatus of claim 1 wherein the tissue condition monitor is one or more sensor or probe that can be either inserted into or taken up by the tissue being measured or can be extraneous to the tissue.

3. The apparatus of claim 1 wherein the tissue condition monitor can collect data from multiple sensors or probes and integrate the data to provide an integrated signal to the reperfusion controller.

4. The apparatus of claim 1 wherein the tissue condition monitor is a tissue oxygen sensor.

5. The apparatus of claim 1 wherein the tissue condition monitor is a molecular probe that is taken up by the injured cells and is configured to undergo a conformational or other type of change that is detectable.

6. The apparatus of claim 1 wherein the reperfusion controller is operable to command the reperfusion generator to generate reperfusate to specified oxygen content.

7. The apparatus of claim 1 wherein the reperfusion controller is operable to compare signals from the tissue condition monitor to a desired tissue parameter level, and operable to command the reperfusion generator to generate reperfusate with a specified oxygen content, flow rate or mixture rate.

8. The apparatus of claim 1 wherein the ischemic tissue being monitored is selected from the group consisting of organs and muscle.

9. The apparatus of claim 1 wherein the reperfusion parameter is at least one of pO2, pH, and Leukocyte Elastase.

10. The apparatus of claim 1 wherein the target therapy curve requires the reperfusate to be delivered at a constant flow rate.

* * * * *